US007629478B2

(12) United States Patent
Soi et al.

(10) Patent No.: US 7,629,478 B2
(45) Date of Patent: Dec. 8, 2009

(54) PROCESS FOR THE PRODUCTION OF A POLYOL MONOMER

(75) Inventors: Hoong Seng Soi, Selangor (MY); Nur Musyahadah Mazalan, Selangor (MY); Mohd Nurhisham Sattar, Selangor (MY); Tuan Noor Mazne Tuan Ismail, Selangor (MY); Hazimah Abu Hassan, Selangor (MY); Ooi Tian Lye, Selangor (MY); Salmiah Ahmad, Selangor (MY); Mohd Basri Wahid, Selangor (MY); Tan Sri Datuk Yusof Basiron, Selangor (MY)

(73) Assignee: Malaysian Palm Oil Board (MPOB), Kajang (MY)

( * ) Notice: Subject to any disclaimer, the term of this patent is extended or adjusted under 35 U.S.C. 154(b) by 0 days.

(21) Appl. No.: 11/557,065

(22) Filed: Nov. 6, 2006

(65) Prior Publication Data

US 2007/0232816 A1    Oct. 4, 2007

(30) Foreign Application Priority Data

Nov. 8, 2005    (MY) .............................. PI 20055231

(51) Int. Cl.
*C07C 303/00*    (2006.01)
(52) U.S. Cl. ..................... 549/513; 549/539; 549/562; 554/145; 554/161; 554/168; 554/173
(58) Field of Classification Search ................. 554/145, 554/161, 173, 168; 549/513, 539, 562
See application file for complete search history.

(56) References Cited

U.S. PATENT DOCUMENTS

| 2,206,168 | A | * | 7/1940 | Edeler et al. ................. 554/168 |
| 2,383,614 | A | * | 8/1945 | Percy ......................... 554/167 |
| 2,744,124 | A | * | 5/1956 | Alsop ........................ 554/168 |
| 2,909,540 | A | * | 10/1959 | Woods ....................... 554/168 |
| 3,050,481 | A | * | 8/1962 | Ault et al. .................. 524/114 |
| 3,637,539 | A |   | 1/1972 | Wolff et al. |
| 4,886,893 | A | * | 12/1989 | Meffert et al. .............. 549/562 |
| 5,380,886 | A | * | 1/1995 | Daute et al. ................. 549/539 |
| 6,107,433 | A | * | 8/2000 | Petrovic et al. ................ 528/1 |

FOREIGN PATENT DOCUMENTS

GB                908500            10/1962

OTHER PUBLICATIONS

Findley et al., "Epoxidation of Unsaturated Fatty Materials with Peracetic Acid in Glacial Acetic Acid", 1945, Journal of American Chemical Society, vol. 67, pp. 413, 414.*
Pouilloux, Y. et al. , Synthesis of glycerol monooctadecanoate from octadecanoic acid and glycerol. Influence of solvent on teh catlytic properties of basic oxides, 2000, Academie des Sciences, chemistry, vol. 3, pp. 589-594.*
Eychenne, et al., High concentration of 1-(3-)monoglycerides by direct partial estrificaton of fatty acids with glycerol, 1999, Fett/Lipid, vol. 101, No. 11, pp. 424-427.*
Scholnick, F. et al., Urethane Foams form Animal Fats. IV. Rigid Foams form Epoxidized Glycerides, 1968, Journal of the American Oil Chemists' Society, vol. 45, No. 2, pp. 76-77.*
Findley, T. et al., Epoxidation of Unsaturated Fatty materials with Peracetic Acid in Glacial Acetic Acid Solution, 1945, Journal of the American Chemical Society, 67(3), pp. 412-414.*
Savary, P., Organic Chemistry—Note on the prepartion of monoglycerides, 1948, Academie des Sciences, pp. 1284-1285.*
Savary, P., Organic Chemistry—Note on the prepartion of monoglycerides, 1948, Academie des Sciences, Eng. Trans. 5 pages.*

* cited by examiner

*Primary Examiner*—Porfirio Nazario-Gonzalez
*Assistant Examiner*—Yate' K Cutliff
(74) *Attorney, Agent, or Firm*—Workman Nydegger

(57) ABSTRACT

A process for preparing palm-based polyol monomer includes reacting unsaturated fatty acids or its corresponding triglycerides with polyhydric alcohol. In particular, one example uses oleic acid with about 70% purity as the starting material for preparing the polyol monomer. Moreover, another example uses refined, bleached, and deodorized (RBD) palm olein as an alternative to oleic acid as the starting material. The preparation of the polyol monomer involves the production of monoglyceride of unsaturated fatty acids, which was further epoxidized with peracid and finally ring opened with polyhydric alcohols. Such polyol monomer is used as a raw material for the production of various types of polyurethane products.

35 Claims, No Drawings

PROCESS FOR THE PRODUCTION OF A POLYOL MONOMER

FIELD OF INVENTION

The present invention relates to a process for the production of a polyol monomer.

BACKGROUND OF INVENTION

A wide range of polyols that is used in polyurethane industries originated from petroleum-based chemicals. Most of the petroleum-based polyols fall into two classes, i.e. hydroxyl-terminated polyethers and hydroxyl-terminated polyesters. The polyesters are prepared by reaction of dibasic acids such as adipic acid, sebacic acid or phthalic acid with diols such as ethylene glycol or with higher functionality alcohols such as glycerol. On the other hand, polyether polyols of most interest in solid polyurethane are the polypropylene glycols and the polytetramethylene glycols. In both cases, the manufacture involves the addition polymerisation of the monomeric epoxide The oil palm industry can be further strengthened through products diversification that can be produced within the sector itself. Currently, 80% of palm oil is utilised in the food industry, whereas only about 20% is utilised in the non-food industries, mainly in the production of oleochemicals such as soap.

Other than surfactants and soaps, vegetable oils like palm oil being triglycerides of fatty acids, have a number of excellent properties which could be utilised in producing valuable polyurethane (PU) products. With the continuous escalation in price of crude oil, polyols based on vegetable oils are increasingly becoming more viable alternatives to the petrochemicals polyols. It is known that PU products are very versatile as they continue to make positive contribution to improve our living standards, whether as automotive components, house-hold furniture, elastomers for shoes, coating materials, sealants or as adhesives.

As the world's petroleum resources are depleting coupled with pressure from environmentalist organisations, scientists worldwide have been looking into renewable/sustainable raw materials to replace petroleum-based polyols. Natural oils, which can be derived from both plants and animals sources, making them an ideal alternative chemical feedstock.

According to Erhlich (1959), the naturally occurring castor oil is the most satisfactory raw material for urethane reaction as the trifunctionality of castor oil contributes to the toughness of the polymer structure and the long chain fatty acid imparts flexibility and water resistance. In order to use other natural oils as polyols for polyurethane production, multiple hydroxyl functionality is required. Hydroxyl functionality naturally occur in castor oil and can be introduced synthetically in other natural oil with unsaturated sites by epoxidation followed by ring opening with alcohols, amino alcohols or acids.

The preparation of polyols from animal and vegetable based triglycerides has been described in many prior art. For an example, U.S. Pat. No. 3,637,539, describes a process whereby a mixture of triglycerides of $C_6$ to $C_{24}$ is heated with dialkanolamine to produce polyols for the production of good quality rigid polyurethane foam.

Bilyk et. al. (1974) claimed that polyols of higher hydroxyl content can be prepared by reacting epoxidised tallow with trimethylolpropane in the presence of p-toluene sulphonic acid.

British patent application (publication no. GB 908500) discloses a process for preparing polyesters from epoxy-containing monoglycerides, in which epoxidised triglycerides are subjected to glycerolysis in the presence of pyridine, resulting a mixture of predominantly epoxidised monoglyceride. The mixture is then reacted with dibasic acids for at least 17 hours at 150° C. to give polyester resins with various physical properties depending on the type of dibasic acids used in the preparation. GB 908500 also described that the preparation of epoxidised triglycerides are done through any known method such as reaction between peracids with the unsaturation of triglycerides. However the common methods of preparing monoglyceride from non-epoxidised glycerides are not readily adaptable to the treatment of epoxidised triglycerides, as the oxirane group will undergo ring opening in the presence of most catalysts generally employed in any known methods for preparing monoglycerides. In addition, it was revealed in GB 908500 that a possible method for obtaining epoxidised partial glycerides by epoxidising a monoglyceride of unsaturated fatty acids is not satisfactory for preparing an epoxidised monoglyceride as the presence of free hydroxyl group on partial glyceride interferes with the epoxidation reaction, which resulted in no appreciable amount of epoxy-containing monoglyceride is formed.

Accordingly, it is an object of this invention to provide such a method of synthesis that produces predominantly monoglyceride from unsaturated fatty acids or its corresponding triglycerides and polyhydric alcohol.

It is a further object of this invention to provide such a method of synthesis that involves epoxidising monoglyceride of unsaturated fatty acids to yield appreciable amount of epoxidised monoglyceride, which prior art has not be able to achieve.

It is another object of this invention to provide such a method of synthesis that converts epoxidised monoglycerides of unsaturated fatty acids to yield polyol monomer by means of ring opening with polyhydric alcohols.

SUMMARY OF INVENTION

Accordingly, there is provided a process for the production of a polyol monomer, the process includes (a) reacting an unsaturated fatty acid or its corresponding triglycerides with a polyhydric alcohol in the presence of a catalyst and an emulsifier to prepare a monoglyceride, (b) epoxidising unsaturated fatty acids of the said monoglyceride and (c) reacting the epoxidised monoglyceride with a polyhydric alcohol characterised in that steps (a) to (c) are conducted at a temperature of between 30° C. to 180° C. and a pressure of between 0 mbar to 1 bar for a duration of 3 hours to 5 hours.

DETAILED DESCRIPTION OF THE PREFERRED EMBODIMENTS

The present invention relates to a process for the production of a polyol monomer. Hereinafter, this specification will describe the present invention according to the preferred embodiments of the present invention. However, it is to be understood that limiting the description to the preferred embodiments of the invention is merely to facilitate discussion of the present invention and it is envisioned that those skilled in the art may devise various modifications and equivalents without departing from the scope of the appended claims.

The process of the invention relates to the production of a polyol monomer from unsaturated fatty acids or its corresponding triglycerides and polyhydric alcohol. More particularly, the present invention relates to three major steps in preparing polyol monomer, namely the preparation of monoglyceride from unsaturated fatty acids or its corresponding triglycerides and polyhydric alcohol; epoxidation of the unsaturated fatty acids of the said monoglyceride and ring opening of the epoxidised monoglyceride with polyhydric alcohols to yield the polyol monomer.

In this invention, monoglyceride is prepared from unsaturated aliphatic monocarboxylic acids having from 18 to 22 carbon atoms and polyhydric alcohols. Typical unsaturated aliphatic acids, which can be utilised in the process, are oleic acid, linoleic acid, elaidic acid, linolenic acid, eleostearic acid, arachidic acid, behenic acid, erucic acid, lignoceric acid, nervonic acid, ricinoleic acid and the like. These fatty acids could be animal or vegetable based. The invention in this process is demonstrated with oleic acid with 70% purity where the preparation of monooleate is described.

On the other hand, the monoglyceride can also be prepared from triglycerides with unsaturated sites such as, but not limited to, cotton, sunflower, corn, rape, palm, linseed and safflower. The invention in this process is demonstrated with RBD palm olein where the preparation of monooleate is described.

Meanwhile, this invention prescribes the use of polyhydric alcohols from both natural and petrochemical sources such as, but not limited to, glycerol, polyglycerol, pentaerythritol, ethylene glycol, propylene glycol, sorbitol, xylitol, sucrose, D-glucose and fructose. Preferably, the polyhydric alcohols are free from any moisture in order to achieve higher yield of monoglyceride. The amount of polyhydric alcohols used for the process is in ratio with the amount of unsaturated fatty acid or triglycerides, which is about 1 to 6 moles of polyhydric alcohol, is employed per mole of unsaturated fatty acid or triglycerides. The polyhydric alcohol is mixed together with the unsaturated fatty acid or triglycerides in the reaction flask, which is then heated to a certain temperature under certain pressure and in the presence of a catalyst together with or without an emulsifier.

Process condition and other operational details can be widely varied. The reaction temperature for preparing monoglyceride will generally be about 120° C. to 140° C. when utilising unsaturated fatty acids as the starting material but in the case of triglycerides, the reaction temperature will be about 140° C. to 180° C. As commonly known to those skilled in the art, if the reaction temperature is too high, undesirable side reaction will occur, and if the temperature is too low, the reaction requires excessive time to achieve good yield.

It is particularly preferred aspect of the invention, that the reaction between unsaturated fatty acid and polyhydric alcohols be conducted at sub-atmospheric pressure and by such operation the reaction can be driven forward to achieve higher yield of monoglyceride by continuous removal of water formed during the reaction. The desired sub-atmospheric pressure is in the range of 0 to 10 mbar, in which optimum yield of the desired product is observed. Preferably, the reaction between triglycerides and polyhydric alcohols is conducted at atmospheric pressure with nitrogen gas purging in order to avoid darkening the product colour.

It has been reported that monoglyceride can be produced from the reaction between unsaturated fatty acid or triglycerides and polyhydric alcohol without the presence of a catalyst but the yield of monoglyceride is considerably low. Therefore, in this invention an acid catalyst is employed to increase the rate of reaction between unsaturated fatty acid and polyhydric alcohol, while in the reaction between triglycerides and polyhydric alcohol, a basic catalyst is employed together with an emulsifier. In the process, about 0.5 to 10 wt percent, more preferably 0.5 to 1.0 percent catalysts and emulsifier were employed based on unsaturated fatty acid or triglycerides weight. Preferably the acid catalysts are concentrated sulphuric acid and para-toluene sulphonic acid, while the preferred basic catalyst is potassium hydroxide and the preferred emulsifier is a soap of fatty acids.

Preferably, an unsaturated fatty acid is used as the starting material. It is generally desired that at the end of the reaction, the reaction mixture have an acid value of 15 mg KOH per gram sample or below. On the other hand, the progress of the reaction between unsaturated fatty acids or triglycerides and polyhydric alcohol can also be monitored through High Performance Liquid Chromatography (HPLC), whereby the change of composition of the products and reactants can be monitored. For this particular invention, the optimum composition of products obtained from this reaction is 60% monoglyceride, predominantly monooleate and 40% diglyceride of a mixture of fatty acids.

After the reaction is completed, the excessive polyhydric alcohol is removed from the products by means of physical separation. The excessive polyhydric alcohol can be purified and recycle for next production of monoglyceride. Furthermore, the product is neutralised with 50% solution of sodium hydroxide or otherwise the acidity of the product will interfere with the epoxidation of monoglyceride. The yield of the monoglyceride is about 95%.

As mentioned, the neutralised monoglyceride is subjected to epoxidation with peracids such as peracetic acid and performic acid. The amount of peracids used is in ratio with the unsaturation present in the monoglyceride, which is 0.1 mole to 3 moles of peracid, is employed per mole of unsaturation present in the monoglyceride, preferably 2.5 moles to 3.0 moles. The reaction temperature for this second step is maintained at 55° C. to 65° C. in order to optimise the formation of oxirane oxygen in monoglyceride. The epoxidation reaction is considered complete when the oxirane oxygen content (OOC) of the monoglyceride reaches about 3.0%, preferably 3.0% to 3.5%

It is then left to separate into two layers, namely an aqueous layer, which predominantly consists of spent peracids and hydrogen peroxide, while the oily layer consists of unreacted monoglyceride and the desired product. The epoxidised monoglyceride is then separated from the aqueous layer and then it is washed with deionised water, followed by a solution of sodium carbonate or sodium hydrogen carbonate until it is neutralised.

Then, it is again washed with deionised water in order to remove the carbonate solution. In the following step, the treated product is mixed with sodium sulphate anhydrous and is left overnight in the oven at 60° C. in order to remove moisture from product. The desired level of moisture retained in the product falls in the range of 0.1 to 0.5%. While the OOC of the epoxidised monoglyceride should be in the range of 3.0% to 3.5%. The yield of the epoxidised monoglyceride is about 90%.

The dried epoxidised monoglyceride is then mixed with polyhydric alcohol with the aid of motorised stirrer and then is heated up to 150° C. to 170° C. for 3 to 5 hours with nitrogen gas purging to produce the final desired product, which is the polyol monomer from fatty acids and polyhydric alcohol. The decrease of OOC of the reactants mixture is monitored. The OOC reaches the 0.5% value, then the reaction is considered as completed. The amount of polyhydric alcohol used for the process is in ratio with the amount of OOC present in the epoxidised monoglyceride, which is about 1.0 to 1.2 moles of polyhydric alcohol, preferably 1.2 moles is employed per mole of epoxidised unsaturation calculated from the oxirane oxygen content. At the end of the process, the desired polyol monomer is a semi-liquid, which is slightly yellowish with a range of viscosity from 20,000 cP to 30,000 cP at 25° C.

Another method for preparing polyol monomer from the dried epoxidised monoglyceride involves ring opening the epoxidised monoglyceride with polyhydric alcohol in the presence of $BF_3$ catalyst at temperature in the range of 90° C. to 100° C. In the same manner, the progress of the reaction can be followed by monitoring descend of OOC of the reactants mixture. The amount of polyhydric alcohol used for the process is in ratio with the amount of OOC present in the epoxidised monoglyceride, which is about 0.5 to 1 mole of polyhydric alcohol, preferably 1.0 mole is employed per mole of epoxidised unsaturation calculated from the oxirane oxygen content. In the process, about 0.1 to 10 wt percent and, more preferably 0.1 to 0.5 percent $BF_3$ catalysts were employed based on the dried epoxidised monoglyceride weight.

Upon completion of the process, the product is subjected to certain analysis to determine its properties. As the results, the hydroxyl value of the polyol monomer falls in the range of 400 to 600 mg KOH per gram sample. In addition, the acid value for the product is about 0.5 to 1.0 mg KOH per gram sample, while the iodine value (IV) for the final product is about 5 to 10 g $I_2$ per 100 g sample, indicating some unsaturation in the raw material still remained in the product. The saponification value of 160 to 170 mg KOH per gram sample indicates the presence of monoglyceride and diglyceride. The moisture content of the product still remains in the range of 0.1% to 0.5%. The final yield of the desired product is about 95%. Referring to these results, the polyol monomer prepared is suitable to be used as raw material for the production of resins suitable for various polyurethane products.

The following examples are intended to further illustrate the invention, without any intent for the present invention to be limited to the specific embodiments described therein.

EXAMPLE 1

6000 g of oleic acid with 74% purity was charged into a 25 L reaction vessel and then 12 kg of anhydrous glycerol was charged into the same vessel together with 30 g of para toluene sulphonic acid as the catalyst. The mixture was then stirred and heated up to 130° C. to 140° C. for 5 hours. The pressure of the vessel was kept at 5 mbar to 10 mbar throughout the reaction by the aid of a vacuum pump in order to drive the reaction forward by removing water formed during the reaction. Then, the acid value of the reaction mixture is analysed. Through HPLC, the disappearance of oleic acid and the emergence of monoglyceride and diglyceride will be monitored. The reaction was considered as completed when the acid value reached 15 mg KOH per gram sample and the composition of monoglyceride and diglyceride was in the ratio of 60% monoglyceride to 40% diglyceride. The mixture was left to separate and the excess glycerol was drawn off from the product. The product was later neutralised with 50% NaOH solution. The yield of the monoglyceride was about 95%.

EXAMPLE 2

59 g of palm olein was charged into a 5 L reaction vessel and then 1656 g of anhydrous glycerol was charged into the same vessel together with 13 g of potassium hydroxide as the catalyst and 13 g of sodium palmitate as the emulsifier. The mixture was then stirred and heated up to 170° C. to 180° C. for 3 hours. The reaction was conducted at atmospheric pressure with nitrogen gas purging in order to avoid the darkening of the product colour. The reaction was followed through HPLC, in which the disappearance of triglycerides and the emergence of monoglyceride and diglyceride were monitored. The reaction was considered as completed when the composition of monoglyceride and diglyceride was in the ratio of 60% monoglyceride to 40% diglyceride. The mixture was left to separate and the excess glycerol was drawn off from the product. The product was later neutralised with 50% NaOH solution. The yield of the monoglyceride was about 95%.

EXAMPLE 3

3 kg of the prepared monoglyceride was charged into a 10 L reaction vessel together with 418.6 g of formic acid. While the mixture was stirred, 1547 g of hydrogen peroxide with 50% purity was slowly added to the same vessel (drop-wise). Epoxidation of the monoglyceride was conducted at temperature 55° C. to 65° C. for about 3 hours. The epoxidation reaction was completed when the OOC of the monoglyceride reached about 3.0%. The epoxidised monoglyceride was separated from the spent acid and then washed with deionised water, followed by sodium carbonate solution until it was neutralised. Following that, the neutralised epoxidised monogyceride was washed again with deionised water in order to remove the residue of sodium carbonate. Later on, the neutralised epoxidised monoglyceride was dried overnight with anhydrous sodium sulphate. The moisture level in the product after drying was 0.5% and the OOC was 3.27%. The yield of the epoxidised monoglyceride was about 91%.

EXAMPLE 4

2845 g of dried and neutralised epoxidised monoglyceride with OOC of 3.27% and moisture content of 0.5% was mixed with 535 g of glycerol in a 5-liter reactor flask. The mixture was stirred and heated to 150° C. to 170° C. for 4 to 5 hours with nitrogen gas purging. During the reaction, the OOC decreases from the initial value of 3.27% to about 1%, indicating ring opening with glycerol. The final product was analysed and the hydroxyl value for the product was in the range of 400 to 600 mg KOH per gram sample while the acid value was about 0.5 to 1.0 mg KOH per gram sample. The IV for the final product is about 5 to 10 g $I_2$ per 100 g sample, indicating some unsaturation in the raw material still remained in the product. Meanwhile, the moisture content of the product still remains in the range of 0.1% to 0.5% and the final OOC of the product was about 0%, which indicates that the epoxy ring in the monoglyceride was fully reacted. The final yield of the desired product was about 94%.

EXAMPLE 5

1 kg of dried and neutralised epoxidised monoglyceride with OOC of 2.3% and moisture content of 0.5% was mixed with 174 g of $BF_3$-glycerol complex in a 5-liter reactor flask. The mixture was stirred and heated to 90° C. to 100° C. for 2 to 3 hours with nitrogen gas purging. During the reaction, the OOC decreases from the initial value of 2.3% to about 0%, indicating ring opening with glycerol. The final product was analysed and the hydroxyl value for the product was in the range of 400 to 600 mg KOH per gram sample while the acid value was about 0.5 to 1.0 mg KOH per gram sample. The IV for the final product is about 5 to 10 g $I_2$ per 100 g sample, indicating some unsaturation in the raw material still remained in the product.

Meanwhile, the moisture content of the product still remains in the range of 0.1% to 0.5% and the final OOC of the product was about 0%, which indicates that the epoxy ring in the monoglyceride was fully reacted. The final yield of the desired product was about 94%.

What is claimed is:

1. A process for producing a polyol monomer, the process comprising:
   (a) reacting at least one of the following:
      an unsaturated fatty acid with a polyhydric alcohol in the presence of an acid catalyst to prepare an unsaturated monoglyceride; or
      a corresponding unsaturated triglyceride of the unsaturated fatty acid with a polyhydric alcohol in the presence of a basic catalyst and an emulsifier to prepare an unsaturated monoglyceride;
   (b) epoxidising the unsaturated monoglyceride of the unsaturated fatty acid or triglyceride; and
   (c) reacting the epoxidised monoglyceride with a polyhydric alcohol to obtain a polyol monomer based on the unsaturated fatty acid or triglyceride,
wherein each of steps (a) through (c) are conducted at a temperature of between about 30° C. to about 180° C. and a pressure of between 0 mbar to about 1 bar for a duration of about 3 hours to about 5 hours.

2. The process according to claim 1, wherein the fatty acid has a total number of carbon atoms which vary from 12 to 22.

3. The process according to claim 1, wherein the fatty acid has a total number of carbon atoms which vary from 18 to 22.

4. The process according to claim 1, wherein the mole ratio between fatty acid or triglycerides and polyhydric alcohol is about 2 to about 6 moles of polyhydric alcohol per mole of fatty acid or triglycerides.

5. The process according to claim 1, wherein the mole ratio between fatty acid or triglycerides and polyhydric alcohol is about 4 to about 6 moles of polyhydric alcohol per mole of fatty acid or triglycerides.

6. The process according to claim 1, wherein the triglycerides are selected from a group consisting of palm oil, cotton oil, sunflower oil, olive oil, corn oil, rape oil, linseed oil, and safflower oil.

7. The process according to claim 1, wherein the triglycerides are selected from a group consisting of crude palm oil; refined, bleached, and deodorized palm oil; and refined, bleached, and deodorized palm olein.

8. The process according to claim 1, wherein the polyhydric alcohol is free from any moisture.

9. The process according to claim 8, wherein the polyhydric alcohol is selected from a group consisting of glycerol, polyglycerol, pentaerythritol, ethylene glycol, propylene glycol, trimethylolpropane, sorbitol, xylitol, sucrose, D-glucose, and fructose.

10. The process according to claim 1, wherein the acid catalyst is an esterification catalyst selected from a group consisting of para toluene sulfuric acid and sulfuric acid.

11. The process according to claim 10, wherein the amount of catalyst employed is about 0.1% to about 10% by weight.

12. The process according to claim 10, wherein the amount of catalyst employed is about 0.5% by weight.

13. The process according to claim 1, wherein the basic catalyst is selected from a group consisting of potassium hydroxide, calcium hydroxide, sodium hydroxide, and lithium hydroxide.

14. The process according to claim 13, wherein the amount of catalyst employed is about 0.1% to about 10% by weight.

15. The process according to claim 13, wherein the amount of catalyst employed is about 0.5% by weight.

16. The process according to claim 1, wherein the acid catalyst is a Lewis acid selected from a group consisting of boron trifluoride, stanum tetrachloride, titanium tetrachloride, and titanium tetrabutoxide.

17. The process according to claim 16, wherein the amount of catalyst employed is about 0.1% to about 10% by weight.

18. The process according to claim 16, wherein the amount of catalyst employed is about 0.4% by weight.

19. The process according to claim 1, wherein the emulsifier employed is a soap of fatty acids selected from a group consisting of sodium laurate, sodium palmitate, and sodium stearate.

20. The process according to claim 1, wherein the amount of emulsifier employed is about 0.5% to about 10% by weight.

21. The process according to claim 1, wherein the amount of emulsifier employed is about 0.5% by weight.

22. The process according to claim 1, wherein steps (a) and (c) are conducted at atmospheric pressure with nitrogen gas purging.

23. The process according to claim 1, wherein the polyol monomer has a hydroxyl number in the range of about 300 to about 600 mg KOH per gram sample.

24. The process according to claim 1, wherein the polyol monomer has a hydroxyl number in the range of about 400 to about 600 mg KOH per gram sample.

25. The process according to claim 1, wherein the polyol monomer has an acid value of about 0.1 to about 1.0 mg KOH per gram sample.

26. The process according to claim 1, wherein the polyol monomer has an acid value of about 0.1 to about 0.2 mg KOH per gram sample.

27. The process according to claim 1, wherein the polyol monomer has a moisture level of about 0.1% to about 0.5% by weight.

28. The process according to claim 1, wherein the polyol monomer has a moisture level of about 0.1% to about 0.2% by weight.

29. The process according to claim 1, wherein the polyol monomer has an iodine value of 5 to 10 g $I_2$ per 100 g sample.

30. The process according to claim 1, wherein the fatty acid is selected from a group consisting of vegetable oils and animal oils.

31. A process for producing a polyol monomer, the process comprising:
   (a) reacting at least one of the following:
      an unsaturated fatty acid with a polyhydric alcohol in the presence of an acid catalyst to prepare an unsaturated monoglyceride; or
      a corresponding unsaturated triglyceride of the unsaturated fatty acid with a polyhydric alcohol in the presence of a basic catalyst and an emulsifier to prepare an unsaturated monoglyceride;
   (b) epoxidising the unsaturated monoglyceride of the unsaturated fatty acid or triglyceride; and
   (c) reacting the epoxidised monoglyceride with a polyhydric alcohol to obtain a polyol monomer based on the unsaturated fatty acid or triglyceride,
wherein steps (a) through (c) are conducted at a temperature of between about 30° C. to about 180° C. and a pressure of between 0 mbar to about 1 bar for a duration of about 3 hours to about 5 hours, said process being characterized by the polyhydric alcohol of step (c) being free of any moisture.

32. The process according to claim 31, wherein the polyol monomer has a hydroxyl number in the range of about 400 to about 600 mg KOH per gram sample.

33. The process according to claim 31, the polyol monomer has an acid value of about 0.1 to about 0.2 mg KOH per gram sample.

34. A process for producing a polyol monomer, the process comprising:
  (a) reacting at least one of the following:
    an unsaturated fatty acid with a polyhydric alcohol in the presence of an acid catalyst to prepare an unsaturated monoglyceride at 120° C. to 140° C. and between 0 mbar and 1 bar for 3 hours to 5 hours; or
    a corresponding unsaturated triglyceride of the unsaturated fatty acid with a polyhydric alcohol in the presence of a basic catalyst and an emulsifier to prepare an unsaturated monoglyceride at 140° C. to 180° C. and between 0 mbar and 1 bar for 3 hours to 5 hours;
  (b) epoxidising the unsaturated monoglyceride of the unsaturated fatty acid or triglyceride at 55° C. to 65° C. and between 0 mbar and 1 bar for 3 hours to 5 hours; and
  (c) reacting the epoxidised monoglyceride with a polyhydric alcohol to obtain a polyol monomer based on the unsaturated fatty acid or triglyceride at 90° C. to 100° C. and between 0 mbar and 1 bar for 3 hours to 5 hours.

35. A process for producing a polyol monomer, the process comprising:
  (a) reacting an unsaturated fatty acid with a polyhydric alcohol in the presence of an acid catalyst to prepare an unsaturated monoglyceride;
  (b) epoxidising the unsaturated monoglyceride of the unsaturated fatty acid; and
  (c) reacting the epoxidised monoglyceride with a polyhydric alcohol to obtain a polyol monomer based on the unsaturated fatty acid,
wherein each of steps (a) through (c) are conducted at a temperature of between about 30° C. to about 180° C. and a pressure of between 0 mbar to about 1 bar for a duration of about 3 hours to about 5 hours.

* * * * *

UNITED STATES PATENT AND TRADEMARK OFFICE
CERTIFICATE OF CORRECTION

PATENT NO. : 7,629,478 B2  Page 1 of 1
APPLICATION NO. : 11/557065
DATED : December 8, 2009
INVENTOR(S) : Soi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 198 days.

Signed and Sealed this

Second Day of November, 2010

David J. Kappos
*Director of the United States Patent and Trademark Office*